United States Patent [19]
Gordaliza et al.

[11] Patent Number: 5,834,507
[45] Date of Patent: Nov. 10, 1998

[54] ANTINEOPLASTIC CYCLOLIGNAN DERIVATIVES

[75] Inventors: Marina Gordaliza; Maria Angeles Castro; Arturo San Feliciano; Jose Maria Miguel del Corral; Maria Luisa Lopez, all of Salamanca; Dolores G. Gravalos, Madrid, all of Spain

[73] Assignee: Universidad de Salamanca, Salamanca, Spain

[21] Appl. No.: 987,925

[22] Filed: Dec. 10, 1997

Related U.S. Application Data

[63] Continuation of Ser. No. 558,128, Nov. 13, 1995, Pat. No. 5,747,529.

[30] Foreign Application Priority Data

Nov. 14, 1994 [GB] United Kingdom .................. 9422946

[51] Int. Cl.$^6$ ........................ A61K 31/36; C07D 317/70
[52] U.S. Cl. ............................. 514/463; 549/433
[58] Field of Search .............. 549/443; 514/463

[56] References Cited

PUBLICATIONS

Hartwell and Schrecker, "The Chemistry of Podophyllum", *Progress in the Chemistry of Organic Natural Products*, pp. 84–166, 1957.

Terada et al., "Antitumor Agents. I. DNA Topoisomerase II Inhibitory Activity and the Structural Relationship of Podophyllotoxin Derivatives as Antitumor Agents", *Chem. Pharm. Bull.*, 40(10) 2720–2727, 1992.

Thurston et al., "Antitumor Agents. 78. Inhibition of Human DNA Topoisomerase II by Podophyllotoxin and α–Peltatin Analogues", *J. Med. Chem.*, 29:1547–1550, 1986.

Rai et al, Chemical Abstracts, 105:164568, (1986).

Rai et al., Current Science, (1986), 55(15), 702–6.

Jones et al., J. Chem. Soc., Perkin Transactions 1, 21, 2541–8, (1993).

*Primary Examiner*—Fiona T. Powers
*Attorney, Agent, or Firm*—Ernest V. Linek; Dike, Bronstein, Roberts & Cushman, LLP

[57] ABSTRACT

Antineoplastic cyclolignan derivatives are of formula (I):

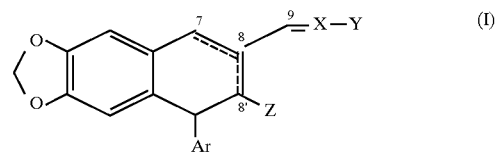

in which

Ar is a 3,4,5-trialkoxyphenyl or 4-hydroxy-3,5-dialkoxyphenyl; X is an oxygen, sulphur or nitrogen atom, a methine group =CH— or an alkylmethine group =C(alkyl)—; Y is a hydrogen atom or an alkyl, alkenyl, (poly)haloalkyl, aryl, hydroxy, alkoxy, amino, monoalkylamino, dialkylamino, (poly)haloalkylamino, arylamino, acyl or acetamido group, or the group Y is absent; Z is an alkyl, hydroxyalkyl, acyl, carboxy, alkoxycarbonyl or aryloxycarbonyl group; and the dotted lines indicate one double bond located at position $\Delta^{7-8}$ or $\Delta^{8-8'}$.

3 Claims, No Drawings

ANTINEOPLASTIC CYCLOLIGNAN DERIVATIVES

CROSS-REFERENCE TO RELATE APPLICATION

This application is a continuation filed under Rule 53(b) (37 C.F.R. 1.53(b)) of copending application Ser. No. 08/558,128, filed Nov. 13, 1995, now U.S. Pat. No. 5,747,529, the disclosure of which is hereby incorporated herein by reference.

BACKGROUND OF THE INVENTION

This invention is concerned with antineoplastic cyclolignan derivatives, the preparation of such derivatives, and pharmaceutical compositions containing them.

SUMMARY OF THE INVENTION

It has now been found, in accordance with the present invention, that certain new cyclolignan derivatives, as hereinafter defined, possess good selectivity as cytotoxic agents against in vitro cultured human solid tumour cell lines as compared with other lignans.

Accordingly, the invention provides cyclolignan derivatives of the formula (I):

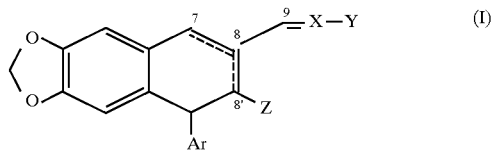

in which
Ar is a 3,4,5-trialkoxyphenyl or 4-hydroxy-3,5-dialkoxyphenyl;
X is an oxygen, sulphur or nitrogen atom, a methine group =CH— or an alkylmethine group =C(alkyl)—;
Y is a hydrogen atom or an alkyl, alkenyl, (poly)haloalkyl, aryl, hydroxy, alkoxy, amino, monoalkylamino, dialkylamino, (poly)haloalkylamino, arylamino, acyl or acetamido group, or the group Y is absent;
Z is an alkyl, hydroxyalkyl, acyl, carboxy, alkoxycarbonyl or aryloxycarbonyl group; and
the dotted lines indicate one double bond located at position $\Delta^{7-8}$ or $\Delta^{8-8'}$.

DETAILED DESCRIPTION OF THE PREFERRED EMBODIMENTS

The alkyl groups preferably have from 1 to 6 carbon atoms, more preferably 1 to 4 carbon atoms. Examples include methyl, ethyl, propyl, isopropyl, butyl, t-butyl and other alkyl groups.

The aryl group is preferably a phenyl or substituted phenyl group. Suitable substituents include the groups given for Y.

The alkoxycarbonyl groups preferably have from 1 to 6 carbon atoms in the alkoxy part, more preferably 1 to 4 carbon atoms. Examples include methoxycarbonyl, ethoxycarbonyl, propoxycarbonyl, isopropoxycarbonyl, butoxycarbonyl, t-butoxycarbonyl and other alkoxycarbonyl groups.

The alkenyl groups preferably have from 3 to 6 carbon atoms, more preferably 3 to 4 carbon atoms. Examples include allyl or crotonyl groups.

The (poly)haloalkyl groups preferably have from 1 to 6 carbon atoms, more preferably 1 to 4 carbon atoms, and preferably have one or more fluoro, chloro or bromo atoms. The (poly)haloalkyl groups are suitably monohalo or perhalo groups. Examples include chloroethyl or trifluoroethyl groups.

The alkoxy groups preferably have from 1 to 6 carbon atoms, more preferably 1 to 4 carbon atoms. Examples include methoxy, ethoxy, propoxy, isopropoxy, butoxy, t-butoxy and other alkoxy groups.

The substituent groups in the substituted amino groups are suitably as described above.

The acyl groups preferably have from 1 to 20 carbon atoms, and more preferably are either short-chain acyl groups with 1 to 3 carbon atoms or long-chain acyl groups with 12 to 18 carbon atoms. The long chain acyl groups may be saturated or unsaturated, preferably of the kind occurring in natural fatty acids. Examples of acyl groups include formyl, acetyl or stearyl.

The aryl group of the arylamino group is suitably as described above.

The hydroxyalkyl groups are preferably 1-hydroxyalkyl groups, have from 1 to 6 carbon atoms, more preferably 1 to 4 carbon atoms.

Examples include hydroxymethyl, 1-hydroxyethyl, 1-hydroxypropyl and other hydroxyalkyl groups.

The aryloxycarbonyl groups preferably have a phenyl or substituted phenyl group.

The present compounds can exist as optical isomers, and the invention embraces the individual isomers and mixtures thereof, including the diastereomeric or racemic mix. The stereochemistry of the substituents may be selected as desired, and for example the group Z can be $\alpha$ or $\beta$.

More generally, the preferred compounds of this invention include compounds of formula (I), wherein one double bond is located at position 7–8 and the function at position 9 is an aldehyde or a hydrazone Individual preferred compounds of this invention include
LL-15, which is methyl 9-deoxy-9-oxo-$\alpha$-apopicropodophyllate.
LL-16, which is the phenylhydrazone of methyl 9-deoxy-9-oxo-$\alpha$-apopicropodophyllate.

The compounds of formula I, as noted above, have cytotoxic activity and, accordingly, the invention also provides cytotoxic pharmaceutical compositions comprising a compound of formula I in association with a pharmaceutical carrier or diluent. Such compositions may, for example, be intended for oral, parenteral or rectal administration in association with suitable appropriate adjuvants. The invention also provides a method for the preparation of a cytotoxic composition which comprises using, as cytotoxic ingredient, a compound of formula I.

The antineoplastic activity of compounds in accordance with this invention is illustrated by the following table, which shows the $IC_{50}$ ($\mu$ g/ml) values for several cyclolignan derivatives against different tumour cell lines.

|  | P-388 | A-549 | HT-29 |
| --- | --- | --- | --- |
| *LL-15 | 0.1 | 0.05 | 0.005 |
| *LL-16 | 1 | 0.5 | 0.02 |
| podophyllotoxin | 0.005 | 0.005 | 0.01 |
| epipodophyllotoxin | 0.5 | 0.1 | 0.1 |

Compounds of the invention may be prepared from podophyllotoxin and related compounds of the Formula (A):

(A) 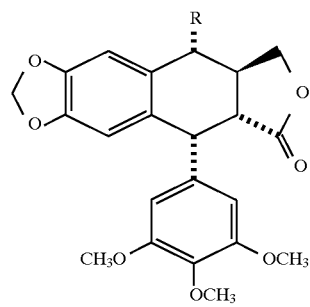

For example, see Hartwell and Schrecker, Fortschrite Chem. Org. Naturstoff 15 83 (1953), which describes podophyllotoxin where R is hydroxy and 8'-H is β; deoxypodophyllotoxin where R is hydrogen and 8'-H is β; and deoxypicropodophyllin where R is hydrogen and 8'-H is α. See also J. Med. Chem. 29 1547–1550 (1986) and Chem. Pharm. Bull. 40 2720–2727 (1992).

The following reaction scheme illustrates the preparation of representative compounds:

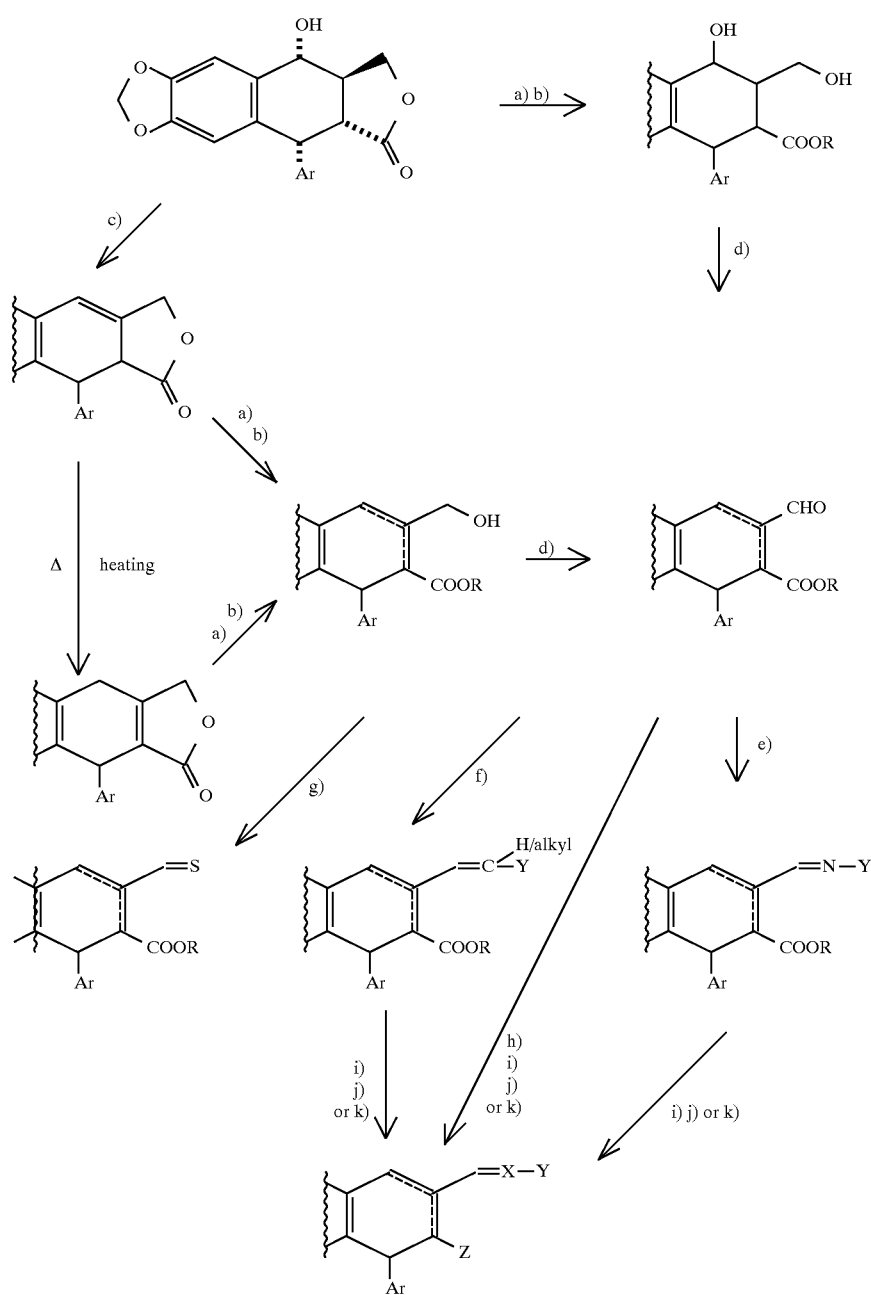

a) KOH/MeOH; b) CH$_2$N$_2$; c) BCl$_3$/C$_6$H$_6$, heating; d) Swern oxidation; e) Y—NH$_2$; f) Wittig Y—C(H/alkyl)=P(phenyl)$_3$; g) Lawesson's reagent h) (MeO)$_2$C(CH$_3$)$_2$, TsOH or HSC$_2$H$_4$SH/BF$_3$; i) LiAlH$_4$; j) acylation; k) Swern oxidation. Other equivalent reaction conditions can be employed, and as appropriate other known starting compounds can be used.

EXAMPLES OF THE INVENTION

In order that the invention may be further understood, the following Examples are given by way of illustration only.

Example 1

Preparation of LL-15

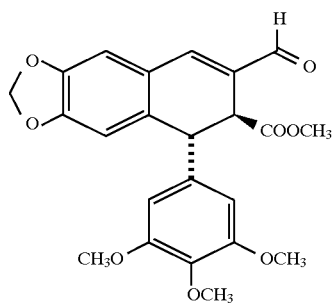

400 mg of podophyllotoxin were dissolved in 30 ml of KOH/MeOH 10% and stirred at room temperature for 30 minutes. After removing the methanol, water was added and the solution was neutralized by 2N HCl until the pH was 7, and then extracted with EtOAc. The reaction product was treated with an ethereal solution of CH$_2$N$_2$ to afford 430 mg of methyl picropodophyllate.

To a precooled (-60° C.) and stirred solution of oxalyl chloride (0.24 ml) in dry CH$_2$Cl$_2$ (5 ml) was added dropwise 0.4 ml of DMSO in CH$_2$Cl$_2$ (2 ml). After 5 minutes at -60° C., a solution of 430 mg of methyl picropodophyllate in 3 ml of CH$_2$Cl$_2$ was slowly added. The reaction mixture was kept at the same temperature for 30 min, then triethylamine (1.27 ml) was added. The mixture was warmed to 0° C. over 1 hour, quenched with water and extracted with CH$_2$Cl$_2$. The reaction product gave 220 mg of LL-15 after flash chromatography.

mp: 72°–74° C.

[α]$_D$(CHCl$_3$): -160.9°

UVλ$_{max}$ (EtOH) (ε): 215(34500), 250 (30000), 358 (26300).

IR(CHCl$_3$)cm$^{-1}$: 3020, 2840, 1740, 1680, 1510, 1240, 1140, 1050

Example 2

Preparation of LL-16

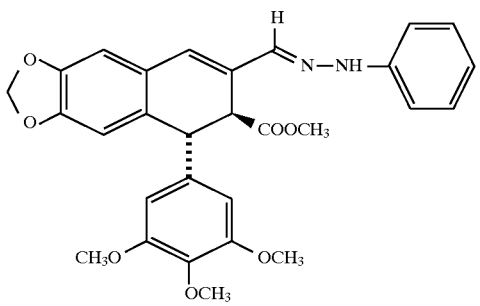

0.1 ml of phenylhydrazine was added to a solution of 180 mg of LL-15 (obtained in Example 1) in 5 ml of glacial acetic acid. The reaction mixture was stirred at room temperature for 7 days. Then water was added and 150 mg of LL-16 were collected.

[M$^+$]: 515 mp: 172°–174° C.

[α]$_D$(CHCl$_3$): -309.1°

UVλ$_{max}$ (EtOH) (ε): 209(28600), 377(24100)

IR(CHCl$_3$) cm$^{-1}$: 3020, 2950, 1740, 1610, 1510, 1260, 1140, 1050

Example 3

Preparation of LL-34, LL-35 and LL-36

0.15 ml of 1,2-ethanedithiol and 3 ml of SiMe$_3$Cl were added to 100 mg of LL-15 in 3 ml of CH$_2$Cl$_2$. After 20 hours at room temperature with stirring under N$_2$ and washing with diluted aq. NaOH, 112 mg of LL-34 were obtained.

To 40 mg of LL-34 in 3 ml of dry ether a suspension of 50 mg of LiAlH$_4$ in dry ether was added. After 3 hours at room temperature and usual working, 37 mg of LL-35 were obtained.

To a solution of 40 mg of HgO and 0.25 ml of BF$_3$Et$_2$O in 5 ml of THF/H$_2$O (85–15) were added 40 mg of LL-35. The mixture was stirred under N$_2$ for 3 hours. Then diluted with CH$_2$Cl$_2$ and the precipitate discarded. The solution after evaporation yielded 30 mg of LL-36.

[α]$_D$ (CHCl$_3$): -85.1°

UVλ$_{max}$(EtOH) (ε): 215 (16500), 245(14300), 356 (8200)

IR (CHCl$_3$) cm$^{-1}$: 3600–3100, 2940, 2860, 1670, 1600, 1510, 1240, 1135, 1045

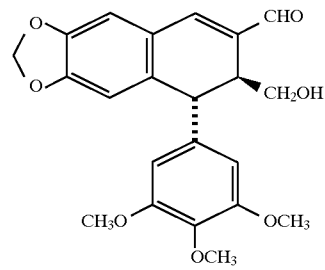

We claim:

1. A compound of formula (I):

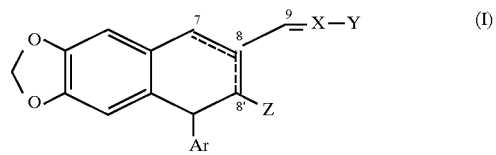

in which

Ar is a 3,4,5-trialkoxyphenyl or 4-hydroxy-3,5-dialkoxyphenyl; and

X is a nitrogen atom;

Y is a hydrogen atom or an alkyl, alkenyl, (poly)haloalkyl, aryl, hydroxy, alkoxy, amino monoalkylamino, dialkylamino, (poly)haloalkylamino, arylamino, acyl or acetamido group, or the group Y is absent;

Z is an alkyl, hydroxyalkyl, acyl, carboxy, alkoxycarbonyl or aryloxycarbonyl group; and the dotted lines indicate one double bond located at position $\Delta^{7-8}$ or $\Delta^{8-8'}$.

2. A pharmaceutical composition which comprises a compound of formula (I):

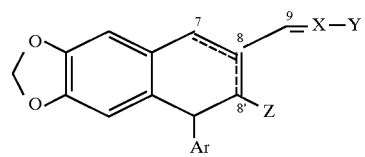
(I)

in which
Ar is a 3,4,5-trialkoxyphenyl or 4-hydroxy-3,5-dialkoxyphenyl; and X is a nitrogen atom;
Y is a hydrogen atom or an alkyl, alkenyl, (poly)haloalkyl, aryl, hydroxy, alkoxy, amino monoalkylamino, dialkylamino, (poly)haloalkylamino, arylamino, acyl or acetamido group, or the group Y is absent;
Z is an alkyl, hydroxyalkyl, acyl, carboxy, alkoxycarbonyl or aryloxycarbonyl group; and
the dotted lines indicate one double bond located at position $\Delta^{7-8}$ or $\Delta^{8-8'}$;
together with a pharmaceutically acceptable carrier.

3. A process for preparing a compound of formula (I):

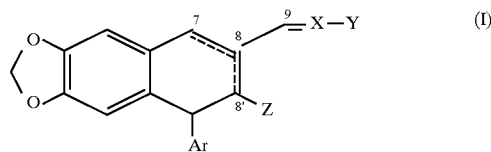
(I)

in which
Ar is a 3,4,5-trialkoxyphenyl or 4-hydroxy-3,5-dialkoxyphenyl; and X is a nitrogen atom;
Y is a hydrogen atom or an alkyl, alkenyl, (poly)haloalkyl, aryl, hydroxy, alkoxy, amino monoalkylamino, dialkylamino, (poly)haloalkylamino, arylamino, acyl or acetamido group, or the group Y is absent;
Z is an alkyl, hydroxyalkyl, acyl, carboxy, alkoxycarbonyl or aryloxycarbonyl group; and
the dotted lines indicate one double bond located at position $\Delta^{7-8}$ or $\Delta^{8-8'}$;
which comprises one or more of the reaction steps shown in the following scheme:

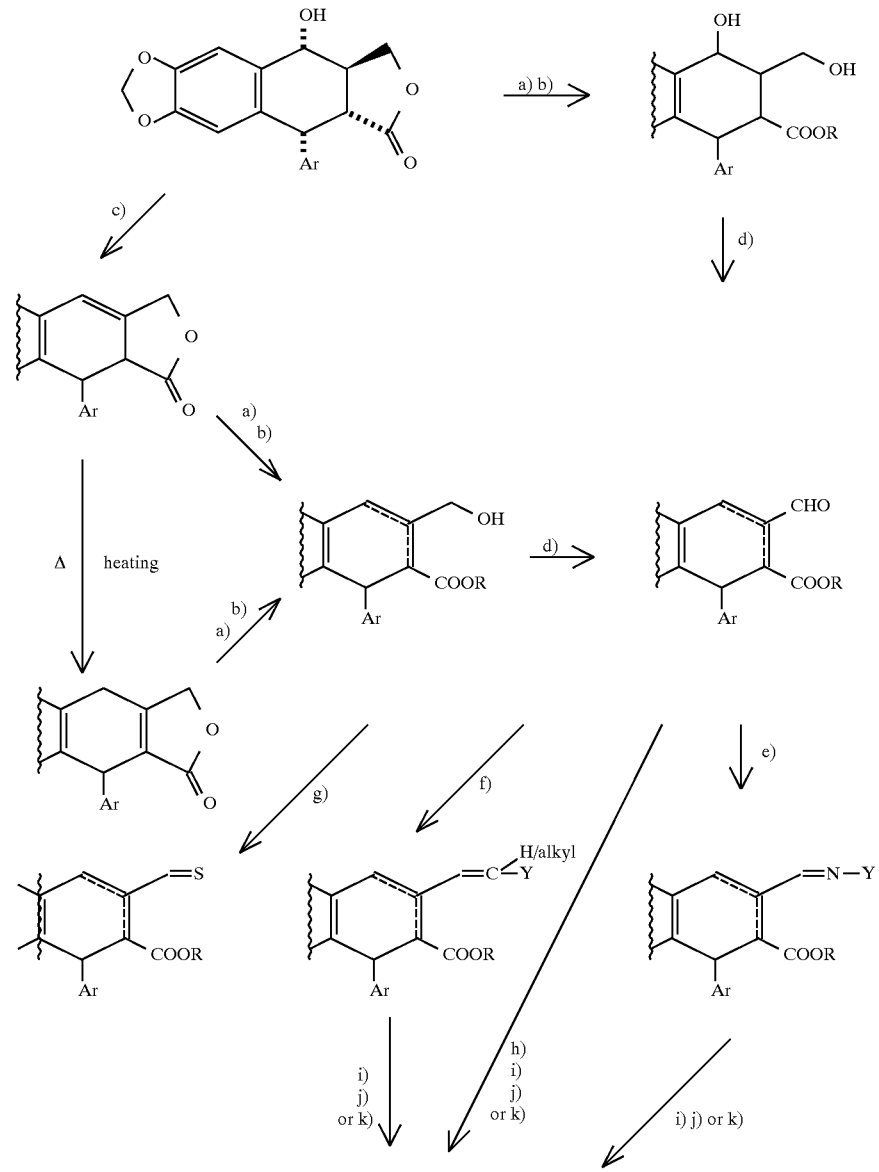

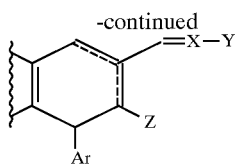
wherein the reaction conditions are identified as follows; (a) KOH/MeOH; (b) $CH_2N_2$; (c) $BCl_3/C_6H_6$, heat; (d) Swern oxidation; (e) Y—$NH_2$; (f) Wittig reaction with Y—C(H/alkyl)=P(phenyl)$_3$; (g) Lawesson's reagent; (h) (MeO)$_2$C(CH$_3$)$_2$, TsOH or HSC$_2$H$_4$SH/BF$_3$; (i) LiAlH$_4$; (j) acylation; (k) Swern oxidation.
* * * * *